United States Patent
Esseiva et al.

(10) Patent No.: US 7,621,445 B2
(45) Date of Patent: Nov. 24, 2009

(54) METHOD AND APPARATUS FOR ACCESS TO HEALTH DATA WITH PORTABLE MEDIA

(75) Inventors: Effron F. D. Esseiva, Bowen Island (CA); Tomer Kol, Yoqneam Illit (IL); Richard J. Stevens, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 311 days.

(21) Appl. No.: 11/530,927

(22) Filed: Sep. 12, 2006

(65) Prior Publication Data

US 2008/0065419 A1 Mar. 13, 2008

(51) Int. Cl.
*G06K 5/00* (2006.01)
(52) U.S. Cl. .......................................... 235/380; 705/3
(58) Field of Classification Search ................. 235/380; 705/3
See application file for complete search history.

(56) References Cited

U.S. PATENT DOCUMENTS 5,924,074 A * 7/1999 Evans ............................ 705/3

6,272,470 B1 * 8/2001 Teshima ......................... 705/3

FOREIGN PATENT DOCUMENTS

| EP | 1077415 A1 | 2/2001 |
|----|------------|--------|
| WO | 99/22330 A1 | 5/1999 |
| WO | 99/44162 A1 | 9/1999 |

* cited by examiner

*Primary Examiner*—Michael G Lee
*Assistant Examiner*—Rafferty Kelly
(74) *Attorney, Agent, or Firm*—Patterson & Sheridan, LLP

(57) ABSTRACT

A method and apparatus for managing electronic medical records is disclosed. One method for managing medical records includes defining a tiered hierarchy of medical record storage categories. A first tier may store electronic medical records for the individual and a second tier may store links to medical records not stored on the portable electronic storage device. Once a collection of electronic records related to an individual is defined, at least some of the records may be stored on a portable electronic storage device (such as a smartcard), according to the tiered hierarchy specified by the record categories.

21 Claims, 4 Drawing Sheets

METHOD AND APPARATUS FOR ACCESS TO HEALTH DATA WITH PORTABLE MEDIA

BACKGROUND OF THE INVENTION

1. Field of the Invention

The present invention generally relates to electronic health records. More specifically, the present invention relates to a methods and apparatus for distributing electronic health records with a portable electronic storage device.

2. Description of the Related Art

Electronic data is pervasive; electronic data records have been created to capture details about almost any conceivable transaction or event. Medical records, for example, contain various data about patients, including medical history data, test data, medication data, etc. Some records may be of critical importance (e.g., a record of an allergy to medication) while other records may be much less significant (e.g., records of a healed injury). Electronic medical records (EMRs) have become a vital resource for doctors, researchers, laboratories, insurance providers, and claims-processors, etc.

One of the problems created by the proliferation of data is the management and accessibility of the data. Currently, EMR's are often stored by multiple unrelated entities, none of which are specialized in providing data storage or retrieval services. For example, a health care provider may maintain an internal set of electronic records for individual patients treated by the provider. Similarly, a pharmacist may maintain records for prescriptions dispensed to a patient at a particular location or pharmacy chain. Another health care provider, however, will not normally have on-demand access to the records of either. As illustrated by even this simple example, the electronic medical records related to a patient may be spread across many entities, and each entity is often limited to accessing EMRs created by that particular entity.

Providing access to a complete collection of electronic medical records from this widely distributed data has proven to be very difficult. One proposed solution for creating a comprehensive EMR system involves creating a data federation. In such a federation, the electronic medical records related to a particular patient may be maintained at individual organizations (e.g., the healthcare provider, pharmacist, clinic, etc.), or at a number of repositories established to consolidate some EMR data. For example, the Cross Enterprise Document Sharing (XDS) profile (defined by the Integrating the Healthcare Enterprise (IHE) organization) is representative of a federated model. The XDS profile describes a clinical domain where institutions that join the domain share electronic medical records with one another. The clinical domain may include one to many data repositories storing electronic medical records.

Such models will typically rely on some form of federated query or retrieval operation when a request is made to view electronic health records for a given patient. That is, federated systems may respond to an EMR data request by (i) identifying each node that may include EMR data for the patient, and (ii) attempting to retrieve the relevant EMR data from each such provider node. Unfortunately, identifying each node that may include EMR data for the patient may be an imprecise process, and may be error prone. Additionally, if the patient previously received care at a facility outside the federation, the results of a federated query may not contain any record of the medical data generated during this care.

Furthermore, during emergency situations, doctors in a treatment center must quickly make life and death decisions. The medical history of a patient, including known allergies and drug interactions may play a large role in these decisions. If the patient has never before received medical care at the particular treatment center, the doctor may not have quick access to the patient's relevant medical history, and performing a comprehensive federated query to locate the necessary medical records may be a time consuming and, as previously described, imprecise process.

Accordingly, what is needed is a versatile method and system for distributing a user's medical data and locations of where further medical data may be found.

SUMMARY OF THE INVENTION

The present invention generally relates to electronic health records. More specifically, the present invention relates to methods for and systems for distributing electronic health records with a portable electronic device.

One embodiment of the invention includes a method of managing medical records. The method generally includes identifying a collection of electronic records related to an individual and storing at least some of the collection of electronic medical records on a portable electronic storage device according to a tiered hierarchy of medical record storage categories. The tiered hierarchy may include patient data for the individual, a first tier for storing electronic medical records for the individual, and a second tier for storing one or more links to medical records not stored on the portable electronic storage device.

Once medical records are available on the portable electronic storage device, the method may further include receiving the portable electronic storage device, and reading the electronic medical records stored on the portable electronic storage device using a storage device reader.

In a particular embodiment, the patient data may include a variety of information such as patient demographic information, allergies, prescriptions, contact information for a primary care physician, a home address, medical conditions, insurance information, and contact information for the patient Another embodiment of the invention includes a computer-readable medium containing a program which, when executed, performs an operation for managing electronic medical records. The operations generally include identifying a collection of electronic records related to an individual; and storing at least some of the collection of electronic medical records on a portable electronic storage device according to a tiered hierarchy of medical record storage categories. The tiered hierarchy may includes patient data for the individual, a first tier for storing electronic medical records for the individual, and a second tier for storing one or more links to medical records not stored on the portable electronic storage device.

Still another embodiment of the invention includes a system. The system may generally include a portable electronic storage device configured to store a collection of electronic records related to an individual according to a tiered hierarchy of medical record storage categories, wherein the tiered hierarchy includes at least patient data for the individual, a first tier for storing electronic medical records for the individual, and a second tier for storing one or more links to medical records not stored on the portable electronic storage device and a reading device configured to access the collection of electronic medical records stored on the portable electronic storage device.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1:
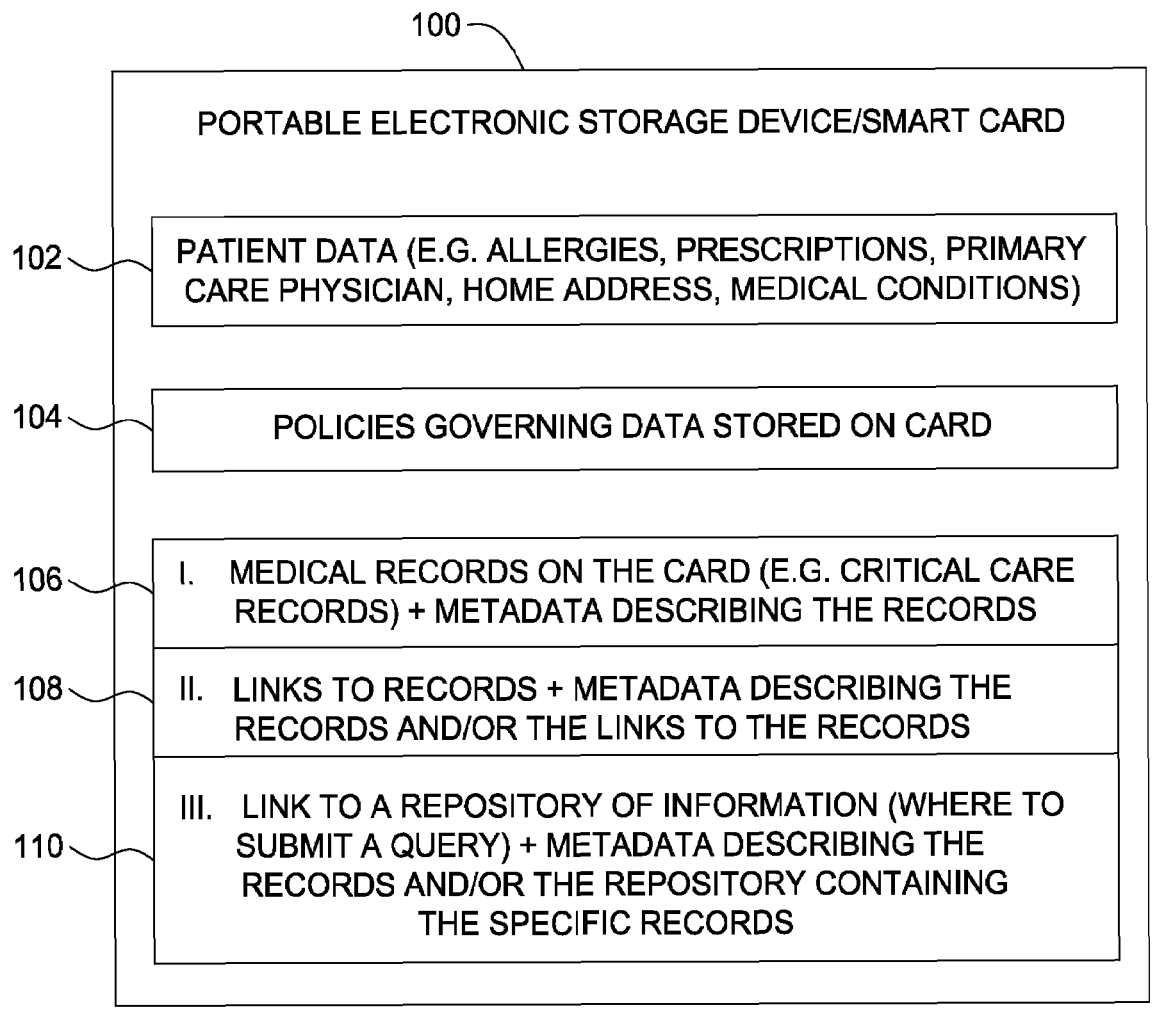
FIG. 1 is a block diagram illustrating a portable electronic storage device containing medical information and links to medical information, according to one embodiment of the invention.

The present invention generally relates to electronic health records. More specifically, the present invention relates to methods for and systems for distributing electronic health records with a portable electronic device.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable media. Illustrative computer-readable media include, but are not limited to: (i) non-writable storage media (e.g., read-only memory devices within a computer such as CD-ROM or DVD-ROM disks readable by a CD- or DVD-ROM drive) on which information is permanently stored; (ii) writable storage media (e.g., floppy disks within a diskette drive or hard-disk drive) on which alterable information is stored. Other media include communications media through which information is conveyed to a computer, such as through a computer or telephone network, including wireless communications networks. The latter embodiment specifically includes transmitting information to/from the Internet and other networks. Such computer-readable media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Personal Electronic Storage Device and Medical Information

As described above, electronic medical records (EMRs) have become a vital resource for doctors, researchers, laboratories, insurance providers, claims-processors, etc. in providing healthcare and healthcare related services. However, in today's medical environment, a given patient may have one or more primary care physicians and a host of specialists, all generating medical information about the patient, and most not sharing such medical information with other physicians. Additionally, a patient may receive medical treatment at several locations, each of which may generate and store records about the patient which may not be accessible at another location. In one embodiment, to resolve management and data accessibility problems created by the proliferation of medical data, the patient may carry a device that contains a hierarchy of medical information.

FIG. 1 is a block diagram illustrating a portable electronic storage device (PESD) 100 containing medical information 102, 106 and links to medical information 108, 110, according to one embodiment of the invention. The PESD 100 may be any portable device capable of storing medical information. Advantageously, the PESD 100 may be a smartcard, which may be credit card-sized and may contain memory and at least one processor. Furthermore, the smartcard may be either a smartcard with electrical contacts for interfacing with a smartcard reader, or may be "contactless," and may utilize RFID (radio-frequency identification) technologies to input and output data. The PESD 100 may store various types of medical information, which may be categorized according to a tiered hierarchy (e.g., critical medical records are stored directly on the PESD 100). By categorizing medical information into tiers, critical medical information may be stored directly on the PESD 100, while less critical information may be stored elsewhere linked from the PESD 100, as is described in more detail below.

Patient Data

In one embodiment, the medical information on the PESD 100 may include patient data 102. Patient data 102 as used herein may refer to demographic information about a patient. Such information may include patient name, a home address, insurance information, and contact information for the patient.

Category I Records

In one embodiment, the medical information stored on PESD 100 may include medical records. Medical records may be any health-related record or information about the patient. For example medical records stored on PESD 100 may be records from a doctor visit, records indicating known allergies, records indicating medical conditions or current medications, organ donor status, a patient's vaccination history, results of a vision test, and/or a patient's prescription history, to name but a few. In one embodiment, medical records may be stored directly on PESD 100. As used herein, these records are called category I records 106 and typically include the patient's highest-priority medical records (e.g. recent critical care records), allergies, and/or chronic conditions (e.g., diabetes), which a physician may use to make important decisions when the patient is in an emergency care situation.

In one embodiment, a category I record 106 may include related metadata, which may give a brief description about the associated medical record. For example, a MRI image stored on the PESD 100 may include the metadata: "MRI of left ventricle illustrating a predisposition for mitral valve prolapse," thus describing the contents of the related image. Additionally, the metadata may include an indication of the priority of a specific medical record so that the physician may easily determine the criticality of the category I record.

Category II Records

In one embodiment, a category II record 108 is a medical record that is not stored on the PESD 100, but rather may be linked from the PESD 100. Storage space on the PESD 100 may be limited; therefore, not every medical record may be stored on the PESD 100. For records that are less critical than category I records 106, or that are simply unable to be stored on the PESD 100, a link to the medical record 108 may be stored on the PESD 100. There are a number of reasons why a medical record may not be able to be stored on the PESD 100, including record size, availability of the information, and record priority. For example, when a patient gives a blood sample during a doctor visit, a thorough laboratory analysis of the blood may not be available for a few days. Therefore, the PESD 100 may be updated during the doctor visit to include a link to the location where the lab results will be stored as well as a date the records should be available. The link to the category II record 108 may be a link to an electronic copy of the associated medical record (e.g., an Internet address). Alternatively, the link may contain a physical location where the record may be found, including contact information of the healthcare provider who has the corresponding record.

In one embodiment, the links to category II records may have associated metadata. Similar to the category I metadata, category II metadata may contain priority information, and may be used by the physician to determine whether the record would be relevant or appropriate to a given situation.

In one embodiment, a record-link, similar to the link to a category II record, may be stored with a category I record. While the link may not be needed as long as the medical record is a category I record (and therefore is stored on the PESD 100), the link may be used if the category I record is ever downgraded to a category II record. Therefore, the removal of the medical record from the PESD 100 may not result in the complete loss of access to the medical data with the PESD 100.

Category III Records

In one embodiment, in addition to medical information stored on the PESD 100 and/or medical information directly linked from the PESD 100, a third category of medical information, category III records 110, includes medical records linked indirectly from the PESD 100. An indirect link may be a reference to a general location which may be queried to locate a patient's medical records. The link may include reference to a particular physician who treated the patient, a hospital where the patient was treated, and/or a region where the patient lived. In a preferred embodiment, the PESD 100 may include a link (e.g., a URL) to an electronic repository containing one or more of the patient's category III medical records 110. The repository may be queried by the user of the storage device reader in order to locate the one or more category III medical records 110. In other words, a category III record is a record stored in a data repository, and a link to the data repository may be stored on PESD 100, whereas a category II record 108 is a record linked directly from the PESD 100.

In one embodiment, the PESD 100 may contain category III metadata related to the category III record(s) 110 contained within the repository. The metadata may contain information about how to communicate with the repository, such as login requirements, system type, accessibility constraints, and/or query parameters. Furthermore, the metadata may describe content of category III medical record(s) 110 contained within the repository as well as record priority, to aid the user of the storage device reader in determining whether to obtain category III medical record(s) 110.

In one embodiment, the presence on the PESD 100 of a link to a repository containing category III medical data may confirm that category III data 110 exists in the repository, and that a query on the repository should return a valid result. Alternatively, the presence on the PESD 100 of a link to a repository containing category III medical data may signify that the repository may contain relevant medical information, but that a query must be performed to determine whether relevant category III data 110 actually exists in the repository.

In one embodiment, a query of the repository may be limited by a healthcare provider to return the most critical category III information and not all records associated with a given patient. Similarly, a query of the repository may be limited to return results pertaining to the capabilities of a physician. For example, when a patient sees an eye doctor, the results from the patient's last visit to the cardiologist may be irrelevant.

In one embodiment, category I and II records 106, 108 have a related electronic storage repository, and therefore a related category III record. Therefore, when updating the PESD 100 with a category I record 106 or a link to a category II record 108, a storage device reader may also include a corresponding link to the category III record, so that reference to the category I or II record 106, 108 will persist on the PESD even after the category I record 106 or a link to the category II record 108 is replaced by a higher priority record or link. In other words, records on the PESD 100 may be dynamic, and including the link to a repository containing a corresponding category III record 110 may improve the utility of the PESD 100.

In one embodiment, physical contact/location information (e.g., addresses, names, and phone numbers) associated with a category II record and/or a category III record may also be stored on the PESD 100. A physician or a user of the storage device reader may use the contact/location information stored on the PESD 100 to contact an originating source of the medical record. Thus, the PESD 100 may facilitate obtaining an electronic medical record (EMR), even when an electronic resource containing the EMR is unavailable.

Data Storage Policy

In one embodiment, the four types of medical data (patient data 102 and category I, II, and III medical records 106, 108, 110) may be used to establish a hierarchy of medical information stored on and/or referenced from the PESD 100. The medical information may be categorized according to a storage policy 104 which governs the type and amount of data and/or links that may be stored on the PESD 100.

In one embodiment, a storage device reader may analyze the storage policy 104, and then organize the medical data accordingly. The storage device reader may use the storage policy 104 to determine whether to update PESD 100 with information associated with a given patient care episode. Furthermore, if there is insufficient storage on the PESD 100, the storage policy 104 may be used to determine which records or references to records to remove from the device, as is described in more detail below. In an alternative embodiment, a processor embedded in the PESD 100 may categorize and organize the medical data stored on and/or linked from the PESD 100 in accordance with the storage policy 104.

In an alternate embodiment, there may be no data storage policy 104 stored on the PESD 100. Rather, the storage policy 104 may be built into the storage device reader. Alternatively, decisions on categorization and storage of medical information may be made by a physician, potentially overriding or supplementing an existing data storage policy 104.

In one embodiment, the data storage policy 104 is static, and cannot be updated. Alternately, the data storage policy 104 may be dynamic and may be updated by a healthcare provider.

Storage Device Reader

Figure 2:
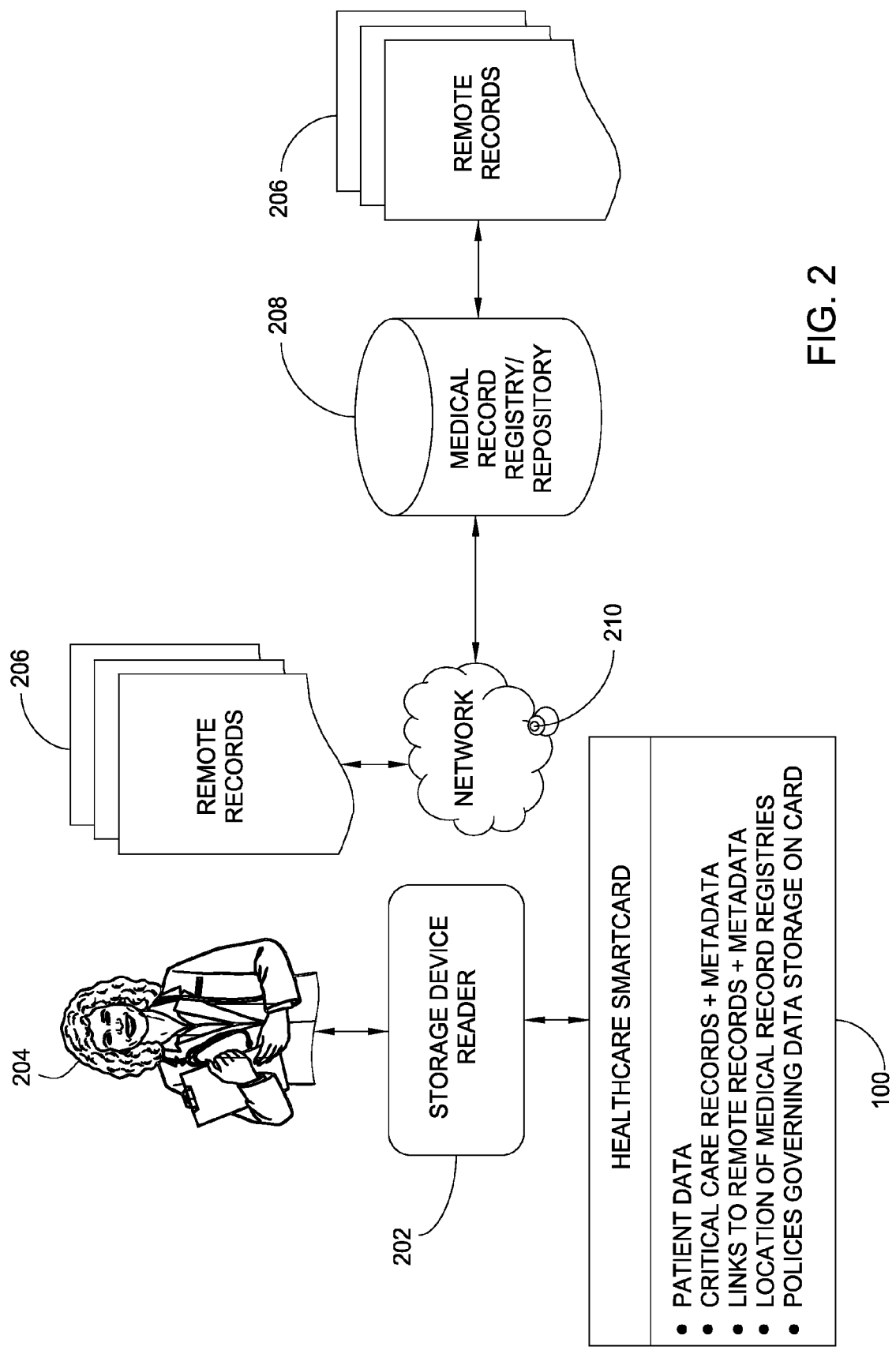
FIG. 2 is a block diagram illustrating a system for reading medical data stored on a portable electronic storage device, and providing a physician with the stored medical data, according to one embodiment of the invention.

FIG. 2 is a block diagram illustrating a system for reading medical data stored on the PESD 100, and providing a user 204 of a storage device reader 202 with the stored medical data, according to one embodiment of the invention. As described above, the storage device reader 202 may be used to access patient data 102, category I medical data 106, category II medical data 108, and category III medical data 110. The storage device reader 202 may include a reader for interfacing with the PESD 100, a screen for displaying the PESD 100 data to the user 204, a network connection for communicating with other sources of medical information over a network 210, and input and output devices.

In one embodiment, the storage device reader 202 may read patient data 102 and category I medical data 106 directly from the PESD 100. Additionally, storage device reader 202 may read a link to category II data 108 on the PESD 100. Reader 202 may then use the link to locate the category II data 108 in a grouping of remote records 206 stored on a network 210. Similarly, storage device reader 202 may read a link to a repository containing category III data 110 on the PESD 100. Reader 202 may use the link to locate the repository/registry 208 containing category III data 110. Storage device reader 202 may then query the repository/registry 208 for relevant category III data 110 stored in a grouping of remote records 206.

In one embodiment, the storage device reader 202 may locate and retrieve category II and III data 108, 110 automatically after locating links to the data on the PESD 100. Alternatively, the storage device reader 202 may report the links and associated metadata to the user 202, and the user 202 may select which records to retrieve via the network 210.

In one embodiment, the storage device reader 202 may not retrieve all the data on the PESD 100, but rather may simply retrieve information pertinent to a specific situation, or may retrieve specific records requested by a doctor. For example, instead of presenting all the data stored on the PESD 100 to a physician, the storage device reader 202 may be configured to return data related to the physician's specialty.

Security/Features

In one embodiment, the PESD 100 may include built-in security protection from misuse of the device, including unauthorized access to information stored on the PESD 100. There are numerous methods for securing information on an electronic device, and all such methods are contemplated for inclusion with the present invention. Illustrative methods for securing information include one or more of: encrypting the data on the PESD 100, including public-key, private-key, and shared-key encryption, where the encryption/decryption is performed by a processor local to the PESD 100 or within the storage device reader 202; requiring a password to access the information stored on the device; restricting access to the PESD 100 to storage device readers 202 containing an updated digital certificate of authenticity; and/or any other traditional and non-traditional security measures. Using one or more of the above described security techniques may prevent theft of a patient's personal and/or medical information if the device is lost or stolen.

Further, the PESD 100 inherently offers security of medical information. Since category II and III medical information 108, 110 are not stored directly on the device, providers of category II and III information 108, 110 may be alerted when a PESD 100 is lost or stolen. Therefore, the providers of category II and III medical records 108, 110 may add additional security measures to be passed before allowing access to a patient's medical records.

In one embodiment, the PESD 100 may include a log file detailing all changes to the information stored on the PESD 100. The log file may be used by a healthcare professional to detect if the device 100 has been tampered with. This may reduce misuse of the PESD 100 by patients, for example, trying to falsely obtain a prescription or other unauthorized medical treatment.

Distribution

The PESD 100 may be a useful tool for management of medical records. However, the benefits of the PESD 100 are reduced if patients do not have access to a PESD 100, or if healthcare providers do not have a storage device reader 202. Accordingly, there are a variety of techniques for distributing the PESD 100 and reader 202 into the hands of patients.

Much like a birth certificate, in one embodiment, everyone may be issued a PESD 100 at birth. The PESD 100 may contain information normally contained on a birth certificate. Furthermore, the PESD may serve as an electronic-birth certificate (e-certificate), and may include a digital authentication system to further validate the e-certificate's authenticity. The e-certificate may be stored in a read-only portion of the PESD 100 to ensure that the e-certificate is never accidentally erased from the PESD 100. Additionally, issuance of the PESD 100 at this early stage of life may aid in establishing a comprehensive medical history on a user's PESD 100.

Given the potential for quick access to patient data 102 and category I records 106, in one embodiment, the PESD 100 may be given by hospitals and/or physicians to critical care patients, high-risk patients, and/or patients with sensitive medical conditions. Therefore, if one of these patients is in a situation requiring rapid or emergency care, relevant information about the patient's medical history may be easily accessible.

In one embodiment, the PESD 100 may be issued to a patient by his/her insurance company. Insurance companies may benefit greatly from the use of the PESD 100, since the added mobility of medical information may reduce duplicative medical procedures and tests, and may therefore save insurance companies the costs of these procedures and tests. Additionally, the insurance companies may issue storage device readers 202 to physicians for the same reason.

In another embodiment, the PESDs 100 and the storage device readers 202 may be offered for sale by a third party, and may be part of a program that patients and healthcare providers opt into. Alternatively, a government sponsored program may control the distribution of PESDs 100 and storage device readers 202.

Regardless of how a patient obtains a PESD 100, to be useful, the PESD 100 should contain information about the patient. Therefore, in one embodiment, the PESD 100 may initially be loaded with patient data 102. Furthermore, the institution providing the PESD 100 may pre-load the PESD 100 with medical data resulting from a federated query of one or more medical record registries 208 for medical records pertaining to the patient. In this manner, the PESD 100 may include medical information about a patient from physician visits and medical tests which occurred long before the patient was issued the PESD 100. As described above, a data storage policy 104 may be used to determine the most appropriate set of medical records to include on the PESD 100. Additionally, a new PESD can be re-issued if an original PESD is damaged or lost. Since the PESD contains a copy of records and links to records, they can be regenerated in the event a new PESD needs to be provided to an individual.

Process for Reading a PESD and Retrieving Medical Records

Figure 3:
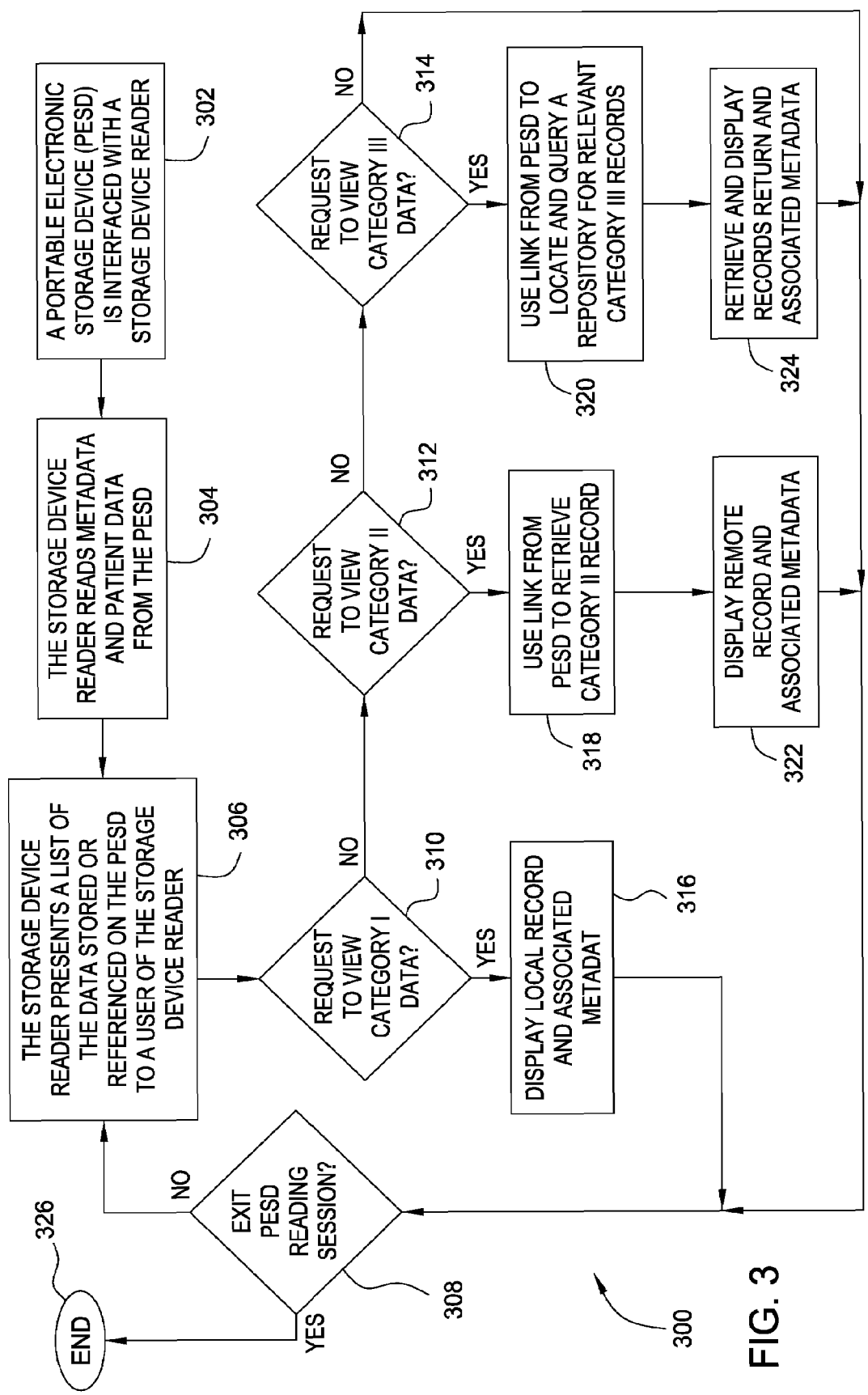
FIG. 3 is a flow diagram illustrating a process for reading information from a portable electronic storage device containing medical information, and retrieving medical records stored or referenced on the portable electronic storage device, according to one embodiment of the invention.

Many factors may influence how the information stored on PESD 100 is read by storage device reader 202. Such factors influencing information retrieval include the presence/lack of a connection to network 210, a medical specialty of the physician retrieving information from PESD 100, and/or the criticality of a individual's medical condition. Therefore, numerous processes may be used for reading medical information from PESD 100. FIG. 3 illustrates one such process.

Process 300 is a process for reading information from a PESD 100 containing medical information and retrieving medical records stored or referenced on the PESD 100, according to one embodiment of the invention. The process 300 begins at step 302, where a PESD 100 is interfaced with a storage device reader. The PESD may be any portable device capable of storing medical information, including a smartcard which may interface with the storage device reader 202 through electrical contacts and/or a "contactless" smartcard which may interface with the storage device reader 202 through RFID technology.

At step 304, the storage device reader 202 reads metadata and patient data 102 from the PESD 100. From the metadata, the storage device reader 202 generates a list of all the data stored on or linked from the PESD 100.

At step 306, the storage device reader 202 presents the list to a user 204 of the storage device reader 202. From this list, the user 204 may select whether to view category I records 106, view category II records 108, view category III records 110, or exit the PESD reading session. Further, the storage device reader 202 may also display all patient data 102 stored on the PESD 100.

At step 310, a determination is made as to whether the user 204 elected to view category I records 106. If the user elected to view category I records 106, at step 316, the records are retrieved from the PESD 100 and presented, along with any related metadata, to the user 204 of the storage device reader 202.

Otherwise, at step 312, a determination is made as to whether the user 204 elected to view category II records 108. If the user elected to view category II records 108, at step 318, storage device reader 202 locates and retrieves records 108 from remote records 206 via network 210. The retrieved records are presented, along with any related metadata, to the user 204 of the storage device reader 202 at step 322.

Otherwise, at step 314, a determination is made as to whether the user 204 elected to view category III records 110. If the user elected to view category III records 110, at step 320, storage device reader 202 locates and queries a medical information repository 208 for relevant medical records. At step 324, the storage device reader 202 retrieves relevant category III records 110 from the repository 208 and presents the retrieved records 110, along with any related metadata, to the user 204 of the storage device reader 202 at step 324.

Whether or not the user 204 elected to view category I, II, and/or III records 106, 108, 110, the storage device reader 202 determines, at step 310, whether the user 204 has elected to exit the PESD 100 reading session. If so, the reading of the PESD 100 terminates at step 326.

Otherwise, processing of the PESD 100 by the storage device reader 202 returns to step 306.

Process for Updating Medical Information on a PESD

Figure 4:
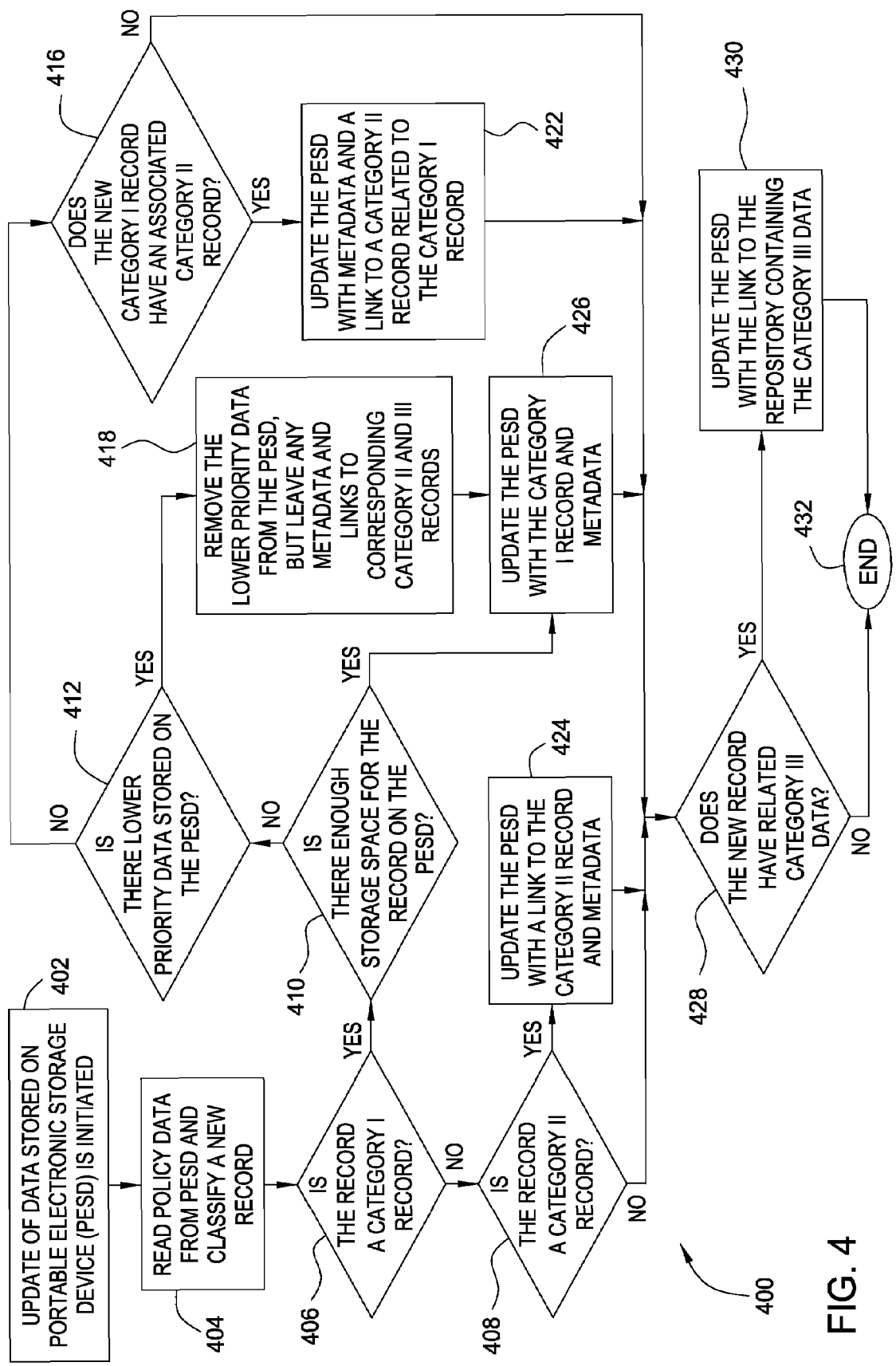
FIG. 4 is a flow diagram illustrating a process for updating medical records information stored on a portable electronic storage device, according to one embodiment of the invention.

FIG. 4 illustrates a process 400 for updating medical information stored on the PESD 100, according to one embodiment of the invention. The process 400 begins at step 402, where an update of the information on the PESD 100 is initiated.

At step 404, the storage card reader 202 reads a data storage policy 104 from PESD 100. Storage card reader 202 then uses data storage policy 104 to classify a new record as a category I, II, or III record 106, 108, 110. Storage card reader 202 determines, at step 406, whether the new record is a category I record 106. If the new record is not a category I reference 106, at step 408 storage card reader 202 determines whether the new record is a category II record 108. As described above, the data storage policy 104 may be contained on the PESD 100, may be stored on the storage card reader 202, or may be specifically dictated by a physician when storing medical records on the device.

If the new record is not a category II reference 108, at step 428, the storage card reader 202 determines whether the new record is or has a related category III reference 110. As described above, category I and II records 106, 108 may have a related storage repository 208, and therefore a related category III record 110. Furthermore, records that do not qualify as category I or II records 106, 108 may also have a related storage repository 208. By always including a link to category III information 110 (when available), a more complete medical profile may be contained on the PESD 100. Therefore, if the new record is or has a related category III reference 110, the PESD 100 is updated with the link to the repository containing the category III data 110 as well as any available metadata at step 430. The process 400 terminates at step 432. It should be noted that the storage on the PESD 100 is limited, and therefore links to older category III references 110 may occasionally need to be removed to make room for links to higher priority category III references 110.

If, at step 428, no category III records 110 were located for the new record, the process 400 terminates at step 432.

If, at step 406, the new record was determined to be a category I reference 106, storage card reader 202 then determines, at step 410, whether there is sufficient space on the PESD 100 for the new record. If there is sufficient storage space on the PESD 100, storage card reader 202 updates PESD 100 with the category I record 106 and related metadata at step 426. Processing of the PESD 100 update continues to step 428, as described above.

Otherwise, if the storage space on the PESD 100 is insufficient, at step 412, the category I records 106 stored on the PESD 100 are reviewed to determine if any existing record has a lower priority than the new category I record 106. If there is an existing record with lower priority, the existing record is removed from the PESD 100 at step 418. However, to preserve reference to the existing record, any links to category II and/or III records 108, 110 related to the existing record, as well as any metadata may be preserved on the PESD 100. As noted, the storage on the PESD 100 is limited; therefore, links to older category II and III references 108, 110 may occasionally need to be removed to make room for links to higher priority category II and III references 108, 110. Processing of the PESD 100 update proceeds to step 426, where, as described above, storage card reader 202 updates PESD 100 with the category I record 106 and related metadata.

If, however, at step 412 no existing category I record 106 has a lower priority than the new record, the storage card reader 202 determines whether the new record has an associated category II reference 108 at step 416. If such a record exists, storage card reader 202 updates PESD 100 with a link to the associated category II reference 108 and related metadata. Processing of the PESD 100 update continues to step 428, as described above.

Otherwise, if there is no category II reference 108 related to the new reference, processing of the PESD 100 update continues to step 428, as described above.

As described above, at step 408, storage card reader 202 determines whether the new record is a category II record 108. If the new record is a category II record 108, storage card reader 202 updates PESD 100 with a link to the category II reference 108 and related metadata. As previously noted, the storage on the PESD 100 is limited, and links to older category II references 108 may occasionally need to be removed to make room for links to higher priority category II references 108. Processing of the PESD 100 update continues to step 428, as described above.

Advantageously, a PESD, such as a smartcard, may be used to manage a patient's medical information. The device may contain medical records and information that can be used to locate additional medical records for the patient. The PESD may be presented by the patient when receiving care and accessed by a physician through a storage device reader. The storage device reader is responsible for reading information stored on the PESD, accessing remote information referenced on the PESD, and updating information on the PESD based on policies for data storage associated with the PESD.

While the foregoing is directed to embodiments of the present invention, other and further embodiments of the invention may be devised without departing from the basic scope thereof, and the scope thereof is determined by the claims that follow.

What is claimed is:

1. A computer implemented method of managing medical records, comprising:
    identifying a collection of electronic records related to an individual; and
    storing at least some of the collection of electronic medical records on a portable electronic storage device having a fixed storage capacity, wherein the electronic records are stored according to a medical record storage policy contained on the portable electronic storage device and specifying a tiered hierarchy of record storage tiers, wherein the tiered hierarchy includes:
        at least a patient data tier for electronic records identifying the individual,
        a first tier for storing, on the portable electronic storage device, copies of electronic medical records related to the individual,
        a second tier for storing one or more links to medical records not stored on the portable electronic storage device, and
        a third tier for storing an indication of one or more repositories of electronic medical records where electronic records related to the individual may be obtained;
    wherein medical records are preferentially stored in the first tier on the portable electronic storage device while space remains available in the fixed storage capacity, according to the medical record storage policy;
    receiving a medical record for storage on the portable electronic storage device, the received medical record not part of the identified collection of electronic records;
    upon determining that the portable electronic storage device has insufficient storage capacity for the received medical record, removing at least one record from a current tier of the first and second tiers; and
    replacing the removed record with a replacement electronic record in a lower tier, of the second and third tiers.

2. The computer implemented method of claim 1, further comprising:
    receiving the portable electronic storage device; and
    reading the patient data for the individual and the medical records stored on the portable electronic storage device using a storage device reader.

3. The computer implemented method of claim 2, further comprising:
    selecting, by a user of the storage device reader, a link to a medical record included in the second tier; and
    retrieving the corresponding medical record from the location specified in the link.

4. The computer implemented method of claim 1, further comprising:
    selecting, by a user of a storage device reader, a link to one of the indicated repositories of medical records included in the third tier; and
    querying the repository of medical records at the location specified by the link to retrieve one or more available electronic records related to the individual.

5. The computer implemented method of claim 1, wherein the patient data includes information related to at least one of allergies, prescriptions, physician contact information, a home address, medical conditions, insurance information, and emergency contact information for the individual.

6. The computer implemented method of claim 1, wherein the policy contained on the portable electronic storage further specifies which medical records in the first tier are stored on the portable electronic storage device and which medical records in the second tier are linked directly from the portable electronic storage device.

7. The computer implemented method of claim 1, wherein the portable electronic storage device is further configured to store metadata associated with the tiered hierarchy of medical records to indicate the content of at least one electronic medical record not directly stored on the portable electronic storage device.

8. The computer implemented method of claim 1, wherein the portable electronic storage device is a smartcard.

9. A computer-readable storage medium containing a program which, when executed, performs an operation for managing electronic medical records, comprising:
    identifying a collection of electronic records related to an individual; and
    storing at least some of the collection of electronic medical records on a portable electronic storage device having a fixed storage capacity, wherein the electronic records are stored according to a medical record storage policy contained on the portable electronic storage device and specifying a tiered hierarchy of record storage tiers, wherein the tiered hierarchy includes:
        at least a patient data tier for electronic records identifying the individual,
        a first tier for storing, on the portable electronic storage device, copies of electronic medical records related to the individual,
        a second tier for storing one or more links to medical records not stored on the portable electronic storage device, and
        a third tier for storing an indication of one or more repositories of electronic medical records where electronic records related to the individual may be obtained; and
    wherein medical records are preferentially stored in the first tier on the portable electronic storage device while space remains available in the fixed storage capacity, according to the medical record storage policy;
    receiving a medical record for storage on the portable electronic storage device, the received medical record not part of the identified collection of electronic records;
    upon determining that the portable electronic storage device has insufficient storage capacity for the received medical record, removing at least one record from a current tier of the first and second tiers; and
    replacing the removed record with a replacement electronic record in a lower tier, of the second and third tiers.

10. The computer-readable storage medium of claim 9, wherein the operations further comprise:
    receiving the portable electronic storage device; and
    reading the patient data for the individual and the medical records stored on the portable electronic storage device using a storage device reader.

11. The computer-readable storage medium of claim 10, wherein the operations further comprise:
    selecting, by a user of the storage device reader, a link to a medical record included in the second tier; and
    retrieving the corresponding medical record from the location specified in the link.

12. The computer-readable storage medium of claim 9, the operations further comprise:
    selecting, by a user of a storage device reader, a link to one of the indicated repositories of medical records included in the third tier; and
    querying the repository of medical records at the location specified by the link to retrieve one or more available electronic records related to the individual.

13. The computer-readable storage medium of claim 9, wherein the patient data includes information related to at least one of allergies, prescriptions, physician contact information, a home address, medical conditions, insurance information, and emergency contact information for the individual.

14. The computer-readable storage medium of claim 9, wherein the policy contained on the portable electronic storage further specifies which medical records in the first tier are stored on the portable electronic storage device and which medical records in the second tier are linked directly from the portable electronic storage device.

15. The computer-readable storage medium of claim 9, wherein the portable electronic storage device is further configured to store metadata associated with the tiered hierarchy of medical records to indicate the content of at least one electronic medical record not directly stored on the portable electronic storage device.

16. The computer-readable storage medium of claim 9, wherein the portable electronic storage device is a smartcard.

17. A system, comprising:
    a portable electronic storage device having a fixed storage capacity configured to store a first collection of electronic records related to an individual, wherein the electronic records are stored according to a medical record storage policy contained on the portable electronic storage device and specifying a tiered hierarchy of record storage tiers, wherein the tiered hierarchy includes:
        at least a patient data tier for electronic records identifying the individual,
        a first tier for storing, on the portable electronic storage device, copies of electronic medical records related to the individual,
        a second tier for storing one or more links to medical records not stored on the portable electronic storage device, and
        a third tier for storing an indication of one or more repositories of electronic medical records where electronic records related to the individual may be obtained; and
    wherein medical records are preferentially stored in the first tier on the portable electronic storage device while space remains available in the fixed storage capacity, according to the medical record storage policy; and
    a reading device configured to:
        access the collection of electronic medical records stored on the portable electronic storage device,
        receive a medical record for storage on the portable electronic storage device, the received medical record not included in the first collection of electronic records;
        upon determining that the portable electronic storage device has insufficient storage capacity for the received medical record, remove at least one record from a current tier of the first and second tiers, and
        replace the removed record with a replacement electronic record in a lower tier, of the second and third tiers.

18. The system of claim 17, wherein the patient data includes information related to at least one of allergies, prescriptions, physician contact information, a home address, medical conditions, insurance information, and emergency contact information for the individual.

19. The system of claim 17, wherein the policy contained on the portable electronic storage further specifies which medical records in the first tier are stored on the portable electronic storage device and which medical records in the second tier are linked directly from the portable electronic storage device in the second tier.

20. The system of claim 17, wherein the portable electronic storage device is further configured to store metadata associated with the tiered hierarchy of medical records to indicate the content of at least one electronic medical record not directly stored on the portable electronic storage device.

21. The system of claim 17, wherein the portable electronic storage device is a smartcard.

* * * * *

UNITED STATES PATENT AND TRADEMARK OFFICE
CERTIFICATE OF CORRECTION

PATENT NO. : 7,621,445 B2 Page 1 of 1
APPLICATION NO. : 11/530927
DATED : November 24, 2009
INVENTOR(S) : Esseiva et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 384 days.

Signed and Sealed this

Twenty-sixth Day of October, 2010

David J. Kappos
*Director of the United States Patent and Trademark Office*